United States Patent [19]

Young

[11] 4,320,229

[45] Mar. 16, 1982

[54] PREPARATION OF ALIPHATIC ALDEHYDES FROM ESTERS

[75] Inventor: Frank G. Young, Charleston, W. Va.

[73] Assignee: Union Carbide Corporation, New York, N.Y.

[21] Appl. No.: 204,023

[22] Filed: Nov. 4, 1980

[51] Int. Cl.³ ..................... C07C 45/27; C07C 47/02
[52] U.S. Cl. ..................................... 568/484; 568/485
[58] Field of Search ...................... 568/485, 489, 484; 564/485

[56] References Cited

U.S. PATENT DOCUMENTS

| | | | |
|---|---|---|---|
| 1,714,783 | 5/1929 | Herrmann et al. | |
| 1,859,786 | 5/1932 | Muller et al. | |
| 2,053,845 | 9/1936 | Schmidt et al. | 260/138 |
| 2,264,812 | 12/1941 | Schulze | 260/549 |
| 3,075,016 | 1/1963 | Hammerberg et al. | 260/595 |
| 3,631,188 | 12/1971 | Wakamatsu et al. | 260/413 |
| 3,639,472 | 2/1972 | Sennewald et al. | 260/541 |
| 3,647,882 | 3/1972 | Roscher et al. | 260/601 R |
| 3,660,416 | 5/1972 | Vlt | 260/297 R |
| 3,721,714 | 3/1973 | Fenton | 260/601 R |
| 3,784,616 | 1/1974 | Fenton | 260/638 R |
| 3,899,539 | 8/1975 | Fernholz et al. | 260/601 R |
| 4,071,563 | 1/1978 | Kummer et al. | 260/601 R |
| 4,093,661 | 6/1978 | Trecker et al. | 260/595 |

*Primary Examiner*—Werren B. Lone
*Attorney, Agent, or Firm*—Bernard Francis Crowe

[57] ABSTRACT

Aliphatic aldehydes are prepared from carboxylic acid esters of primary alcohols by contacting the latter with a wide variety of oxidized elements selected from V, Sb, Mo, and W as well as oxidized element from groups I, III-B, IV, VII-A, and VIII of the periodic system of elements.

10 Claims, No Drawings

PREPARATION OF ALIPHATIC ALDEHYDES FROM ESTERS

BACKGROUND OF THE INVENTION

This invention pertains to the preparation of aliphatic aldehydes from carboxylic acid esters of primary alcohols and more particularly to the use of a catalyst composition having a wide combination of oxidized elements.

Many methods are known in the prior art for the preparation of aliphatic aldehydes such as acetaldehyde. However, with the exception of a note by Meier and Kiefer (Angew. Chem./65, No. 12, page 320, 1953), in which ethyl acetate was converted to acetaldehyde in the presence of basic alumina and 2,4-dinitrophenylhydrazine, the literature describes no other single step process to carry out this reaction. The usual procedure would involve first hydrolysis of for example ethyl acetate to form alcohol and acetic acid. The second step would then involve the reduction of the acetic acid to ethyl alcohol and finally both mols of ethyl alcohol would have to be dehydrogenated to acetaldehyde. Of these steps the chemical reduction is expensive usually requiring a stoichiometric amount of laboratory reductant, for example, lithium-aluminum hydride. All three steps require separate isolation and purification procedures and would increase the overall cost of the preparation of acetaldehyde by this method.

The reverse reaction, the preparation of aliphatic ester from aldehyde, known as the Tishchenko reaction, is conducted using a strong base such as aluminum isopropoxide.

The teaching of Meier et al. specifically teaches that neutral and acid aluminas cannot be used for the purpose of converting ethyl acetate to acetaldehyde.

The early chemical literature teaches that ethyl acetate vapor passed over alumina at elevated temperatures affords acetone, ethylene, carbon dioxide and water. If titania is used, the products are acetic acid and ethylene. If thoria is used, acetone, ethanol, ethylene, and carbon dioxide are formed. (H. Adkins et al., J. Am. Chem. Soc., 44, 385, 1922).

In the presence of nickel and 300°–450° C., ethyl acetate is decomposed to carbon monoxide, carbon dioxide, hydrogen and methane (H. Adkins, Ibid, 44, 2175, 1922).

Bancroft et al. found only ethylene and carbon dioxide when ethyl acetate was passed over alumina (Ibid. 35, 2943, 1931).

When ethyl acetate is oxidized with oxygen in the presence of cobalt naphthenate, the only product is acetic acid in a yield of 80–90% (U.S. Pat. No. 2,530,512; British Pat. No. 643,468, 1950).

When certain oxide catalysts, e.g., CuO,80:Cr$_2$O$_3$,10, are used, oxidation of ethyl acetate at 130°–235° C. in the presence of steam leads only to complete combustion to carbon oxides and water (V. S. Saltanov, Khim, Prom. 44 (5), page 349, 1968; R. P. V. Subba Rao, Zeit. Phys. Chem., 246 (5-6), page 352, 1971).

Fish et al. (J. Chem. Soc. 1963, page 820) indicate that aldehydes are minor products, with acids the major product formed in the noncatalytic (free-radical) oxidation of ethyl acetate. The only reference to a derivative of acetaldehyde as a major product is that of Meier et al. previously cited. In this process not acetaldehyde, but its 2,4-dinitrophenylhydrazone is produced in the absence of reacting oxygen. Formation of this derivative provides the driving force for the reaction and permits a higher, but still very low conversion of ethyl acetate than occurs in its absence.

It is therefore an object of this invention to provide a method for making acetaldehyde and other aliphatic aldehydes from the corresponding aliphatic esters of carboxylic acids in a one-step process which is commercially feasible.

Other objects will become apparent to those skilled in the art upon a further reading of the specification.

SUMMARY OF THE INVENTION

The method of preparing aliphatic aldehydes from carboxylic acid esters of primary alcohols having the formula:

$$RCH_2COOCH_2CH_2R$$

wherein R is hydrogen or an alkyl group having 1 to about 18 carbon atoms, has been devised which comprises contacting said ester with a catalyst composition having the formula:

$$X_aY_b$$

wherein X is 1 or more oxidized elements selected from the group consisting of V, Sb, Mo, and W, and Y is one or more oxidized elements selected from Groups I, III-B, IV, VII-A and VIII of the periodic system of elements, and a and b are each integers having values of 0 to 6 inclusive with the proviso that both a and b cannot be 0 at the same time.

The metal oxides of the present invention permit the formation of acetaldehyde from ethyl acetate in very high yield without the need for the formation of an acetaldehyde derivative. The invention is therefore distinguished from Meier et al. by this property.

The conversion of ethyl acetate to acetaldehyde, as well as the conversion of other like esters, can be carried out at elevated temperatures in either the liquid or vapor phase. Inert diluent gases, such as nitrogen, helium, argon or steam can be used in the gaseous phase and hydrocarbon solvents, such as arenes for example, benzene, toluene, xylene, and the like or paraffins having about 6 to 10 carbons can be used in the liquid phase reactions. The reaction can advantageously be carried out at sub- or super-atmospheric pressures. The higher pressures are preferred for economical recovery of the product acetaldehyde. Atmospheric pressures can also be used if desired. The process can be conducted at complete conversion of the ester or alternatively at lower conversion with separation and recycle of the unreacted ester from the product aldehyde. Reaction temperatures can be in the range of about 50° to about 500° C., and preferably in the range of about 150° to about 300° C.

Dilution with gaseous helium, reaction at subatmospheric (partial) pressure and incomplete ester conversion are preferred modes of operation. The other modes however of practice can also be reasonably employed.

Although ethyl acetate is the preferred carboxylic acid ester used in the practice of this invention, other esters include ethyl propionate, propyl propionate, ethyl butyrate, ethyl pentanoate, ethyl hexanoate, ethyl decanoate, ethyl laurate, butyl myristate, ethyl octadecanoate and the like.

A particularly preferred catalyst is the composition of thallium oxide-vanadium pentoxide having the formula, $Tl_2O—V_2O_5$. This catalyst was found completely unexpectedly during a search for a catalyst to dehydrogenate ethyl acetate efficiently to vinyl acetate and hydrogen. It was found that instead of the intended product this catalyst afforded high selectivity to acetaldehyde from vinyl acetate.

Other useful catalyst compositions falling within the ambit of this invention include:

$V_2Ti_{12}O_{29}$ $V_{48}TIO_{120.5}$ $V_3Sb_{12}O_{25.5}$ $V_3Sb_{12}K_{0.05}O_{25.525}$ $V_3Sb_{12}CeO_{27}$ $W_{3.2}In_{9.6}Si_{2.2}Mo_{16}O_{76.4}$ $CoMn_2Mo_{16}Zr_4O_{72}$ $AgAu_{13.7}O_{21.05}$, and the like.

The selectivity of the catalyst system used in this invention can be shown by the fact that several including vanadium, niobium, molybdenum, thallium, erbium, lanthanum, antimony, palladium, arsenic, magnesium and the like, did not work in various combinations to produce acetaldehyde from an acetate. The delineation of these data is contained in Table III infra.

The invention is further described in the examples which follow. All parts and percentages are by weight unless otherwise specified.

EXAMPLES 1-10

A general procedure was used for demonstrating the effectiveness of various catalyst systems for the preparation of aldehydes from carboxylic acid esters of primary alcohols. This procedure is described below.

The experiments were performed in a U-tubular reactor, close-coupled to a gas-chromatograph analysis device. The reactor, a 40 cm section of 6 mm ($\frac{1}{4}$ inch o.d.) stainless-steel tubing bent in a U-shape, and filled with 6.0 grams of $Tl_2O—V_2O_5$ catalyst, corresponding to the composition $TlV_{16.7}O_{42.25}$, was held in a fluidized sand-bath to heat and control the reaction temperature by means of a thermocouple temperature controller. A canstant supply of helium gas was fed at a rate of 80 ml/min. to the reactor and led therefrom to a gas-chromatograph, equipped with two analysis columns suitable for analyzing reaction products. Ethyl acetate in 3 microliter portions was injected through a rubber system into the helium stream before the catalyst and led over the catalyst under the conditions and with the results tabulated in Table I below. Effluent products were analyzed at 250° C., on a $\frac{1}{4}''\times 10'$ column containing 10 percent SE 30 on Chromosorb W (SE 30 is a silicone gum rubber made by Dow Chemical Co. and Chromosorb W is a calcined diatomaceous earth produced by Johns-Manville Co., Inc.). Under these conditions, retention times were: carbon dioxide, 2.0 min.; acetaldehyde, 2.8 min.; vinyl acetate, 6.3 min.; and ethyl acetate, 9.8 min. For confirmation of the product identity the separated chromatographic peaks were collected and subjected to mass spectrometry and compared with authentic samples of these materials.

Conversion and efficiency calculations were based on the stoichiometry:

$$C_2H_5OCOCH_3 \rightarrow 2CH_3CHO$$

$$C_2H_5OCOCH_3 + 5O_2 \rightarrow 4CO_2 + 4H_2O$$

using chromatographic peak areas, without applying individual response factors. Thus $$\text{Conversion \%} = \frac{100\,(2\text{ Acetaldehyde} + CO_2)}{(2\text{ Acetaldehyde} + CO_2 + 4\text{ Ethyl acetate})}$$

$$\text{Efficiency \%} = \frac{100\,(2\text{ Acetaldehyde})}{(2\text{ Acetaldehyde} + CO_2)}$$

TABLE I

| Example No. | Temperature, °C. | Product Analysis, % | | | Percent | |
|---|---|---|---|---|---|---|
| | | ETAC[1] | AcH[2] | $CO_2$ | Selectivity | Conversion |
| 1 | 110 | 100 | — | — | — | 0 |
| 2 | 150 | 100 | — | — | — | 0 |
| 3 | 218 | 94.3 | 5.7 | — | 100 | 3 |
| 4 | 250 | 89 | 9.7 | 1.3 | 94 | 5.5 |
| 5 | 230 | 94.1 | 5.9 | — | 100 | 3 |
| 6 | 247 | 95.2 | 4.9 | — | 100 | 2.6 |
| 7 | 308 | 61.7 | 26.7 | 11.6 | 82.2 | 21.0 |
| 8 | 356 | 24.1 | 43.8 | 32.1 | 73.1 | 55.4 |
| 9 | 356 | 24.3 | 49.3 | 26.4 | 78.9 | 56.2 |
| 10 | 409 | 0 | 10 | 90 | 18 | 100 |

[1] Ethyl acetate
[2] Acetaldehyde

The catalyst $Tl_2O—V_2O_5$ was prepared as shown below.

Ammonium metavanadate (11.0 grams, 9.4 milliatoms of V) was dissolved in 350 ml of distilled water heated to 90° C., with stirring. Alpha-alumina (Norton Company, lot LA 4102), 50 grams held in an evacuated flask and heated to 90° C. was contacted with the foregoing vanadate solution, while holding the pressure to less than 1 psia so that the solution was evaporated to dryness. The impregnated alumina was then heated in air at 450° C. for 2 hours and cooled. This material was returned to the flask and contacted in the same way as previously with 4.5 grams (2.22 millimoles of Tl) of a 10.9 percent solution of thallous hydroxide diluted to 50 ml with distilled water. The doubly impregnated material was heated in an oven as before for 2 hours and cooled. The finished catalyst analyzed as follows: 2.231% vandium; 0.547% thallium, corresponding to the formula:

$TlV_{16.7}O_{42.25}$.

In the above experiments the helium gas is present as a convenience not a necessity. The reaction can also be conducted by passage of vapors of ethyl acetate, with or without an inert diluent gas such as nitrogen, over the catalyst in a tubular reactor at temperature between about 200° and 400° C. and one atmosphere pressure.

EXAMPLES 11-20

Other catalyst materials falling within the ambit of this invention which afforded acetaldehyde from ethyl acetate using the procedure described above are listed in Table II.

TABLE II

Acetaldehyde from Ethyl Acetate

| Example | Catalyst Composition[1] | Temp., °C. | Conversion, % | Efficiency, % |
|---|---|---|---|---|
| 11 | $V_2Ti_{12}O_{29}$ | 178 | 18.5 | 80.8 |
|  |  | 218 | 19.5 | 94 |
|  |  | 266 | 62.9 | 84 |
| 12 | $V_{48}TiO_{120.5}$ | 218 | 2.9 | 100 |
|  |  | 250 | 5.5 | 94 |
|  |  | 308 | 20.8 | 82.2 |
|  |  | 356 | 55.4 | 73.1 |
|  |  | 409 | 100 | 18 |
| 13 | $V_{48}TiO_{120.5}$[2] | 264 | 3.7 | 83.5 |
|  |  | 290 | 7.8 | 91.4 |
|  |  | 348 | 42.1 | 76.8 |
| 14 | $V_3Sb_{12}O_{25.5}$ | 177 | 6 | 100 |
|  |  | 208 | 8.6 | 98.2 |
|  |  | 227 | 20.7 | 94.9 |
| 15 | $V_3Sb_{12}K_{0.05}O_{25.525}$ | 276 | 3.8 | 97.5 |
|  |  | 298 | 10.7 | 98 |
| 16 | $V_3Sb_{12}CeO_{27}$ | 182 | 9.7 | 100 |
|  |  | 222 | 19.6 | 93.6 |
|  |  | 260 | 26.5 | 85.7 |
|  |  | 305 | 100 | 81 |
| 17 | $W_{3.2}In_{9.6}Si_{2.2}Mo_{16}O_{76.4}$ | 224 | 2.3 | 100 |
|  |  | 264 | 19.8 | 98 |
|  |  | 306 | 27.5 | 94.9 |
| 18 | $Co_{14}Mn_2Mo_{16}Zr_4O_{72}$ | 180 | 29.2 | 100 |
|  |  | 254 | 56.4 | 96.4 |
|  |  | 300 | 100 | 88.3 |
| 19 | $Co_{14}Mn_2Mo_{16}Ti_4O_{72}$ | 250 | 18.6 | 100 |
|  |  | 252 | 17.2 | 100 |
|  |  | 270 | 66.7 | 94.8 |
| 20 | $AgAu_{13.7}O_{21.05}$[4] | 255 | 1.7 | 95.9 |
|  |  | 324 | 0.8 | 100 |
|  |  | 325 | 0.8 | 97 |
|  |  | 362 | 1.8 | 94 |
|  |  | 390 | 2.8 | 88 |
|  |  | 400 | 6.0 | 83 |
|  |  | 402 | 6.1 | 84 |

[1]Mixed metal oxides.
[2]After roasting 20 hours in oxygen at 500° C.
[3]With addition of $TiO_2$.
[4]Oxides not stable at reaction temperatures.

CONTROLS A-G

To demonstrate the metes and bounds of the instant invention a number of Controls were run with similar catalyst systems which did not provide for the formation of either acetaldehyde or vinyl acetate from ethyl acetate. These materials and pertinent remarks are presented in Table III.

TABLE III

Compositions Tested for Formation of Acetaldehyde or Vinyl Acetate from Ethyl Acetate

| Control | Composition | |
|---|---|---|
| A | $V_4Nb_2Mo_{16}O_{63}$ | Complete combustion at 356° C. |
| B | $Tl_2O_3$—$Er_2O_3$ | Complete combustion at 200° C. |
| C | $Tl_2O_3$—$La_2O_3$ | Complete combustion at 200° C. |
| D | $TlSbO_2$ | Complete combustion at 168° C. |
| E | $Pd^{2+}$—$V_2O_5$ | Active above 160° C., no acetaldehyde |
| F | $Tl_3AsO_3$ | Inactive to 222° C. |
| G | $MgMoO_4$ | Inactive to 302° C. |

Although the invention has been described in its preferred forms with a certain degree of particularly, it will be understood by those skilled in the art that the present disclosure has been made only by way of example and that numerous changes can be made without departing from the spirit and the scope of the invention.

What is claimed is:

1. Method of preparing aliphatic aldehydes from carboxylic acid esters of primary alcohols having the formula $$RCH_2COOCH_2CH_2R$$

where R is hydrogen or an alkyl group having 1 to about 18 carbon atoms, which comprises contacting said ester with a catalyst composition having the formula $$X_aY_b$$

where X is one or more oxidized elements selected from the group consisting of V, Sb, Mo and W, Y is one or more oxidized elements selected from Groups I, III-B, IV, VII-A and VIII of the periodic system of elements, and a and b are each integers having values of 0 to 6 inclusive with the proviso that both a and b cannot be 0 at the same time, at a reaction temperature of about 50° to about 500° C. until the desired conversion of ester to aldehyde occurs.

2. Method claimed in claim 1 wherein the reaction temperature is about 150° to about 300° C.

3. Method claimed in claim 1 wherein the carboxylic acid ester is a primary alkyl acetate wherein the alkyl contains at least two carbon atoms.

4. Method claimed in claim 2 wherein the alkyl group is ethyl.

5. Method claimed in claim 1 wherein the catalyst composition having the formula $X_aY_b$ is $Tl_2O$—$V_2O_5$.

6. Method claimed in claim 1 carried out in the liquid phase.

7. Method claimed in claim 1 carried out in the vapor phase.

8. Method claimed in claim 7 wherein reaction is carried out under an inert diluent gas.

9. Method claimed in claim 7 wherein the gas is helium.

10. Method claimed in claim 1 wherein reaction is carried out at sub-atmospheric pressures and incomplete ester conversion to aldehyde is practiced.

* * * * *